US00PP11254P

United States Patent [19]

Boeder

[11] Patent Number: Plant 11,254

[45] Date of Patent: Feb. 29, 2000

[54] CHRYSANTHEMUM PLANT NAMED 'IBIS'

[75] Inventor: Mark Boeder, West Wittering, United Kingdom

[73] Assignee: Cleangro Limited, United Kingdom

[21] Appl. No.: 09/038,766

[22] Filed: Mar. 11, 1998

[51] Int. Cl.[7] ..... A01H 5/00

[52] U.S. Cl. ..... Plt./287

[58] Field of Search ..... Plt./287, 292, 293

[56] References Cited

U.S. PATENT DOCUMENTS

P.P. 9,584 6/1996 Fuess ..... Plt./287
P.P. 10,212 1/1998 Wain ..... Plt./287

*Primary Examiner*—Howard J. Locker
*Attorney, Agent, or Firm*—Christie, Parker & Hale, LLP

[57] ABSTRACT

A new plant variety of chrysanthemum producing magenta flowers with a very slight coral appearance in center.

2 Drawing Sheets

BACKGROUND OF THE INVENTION

The present invention is directed to a new and distinct variety of Chrysanthemum botanically classified as *Dendranthema grandiflora*. The varietal denomination of the new Chrysanthemum is 'Ibis'.

The female parent of the new variety is the variety known as 'Bravo' (U.S. Plant Pat. No. 6,888) and the male parent is an undistributed, unnamed seedling identified as 'G10-C3'. The new variety has been asexually reproduced by vegetative cuttings in Ventura County, Calif. and the distinguishing characteristics are retained through successive generations of asexual reproduction.

SUMMARY OF THE INVENTION

'Ibis' is a pot type Chrysanthemum plant variety that produces magenta flowers with very slight coral appearance in the center.

COMPARISON WITH 'BRAVO'

'Ibis' differs from 'Bravo' in that 'Bravo' has a flower of flat form while 'Ibis' flower form is more spherical. Also, the plant of the new variety is more spreading than 'Bravo'.

BRIEF DESCRIPTION OF ILLUSTRATIONS

The accompanying photographs show a typical specimen of potted plant of the new variety and of flowers of the new variety, with colors being as nearly true as possible with illustrations of this type.

DESCRIPTION OF THE PLANT

Figure 1:
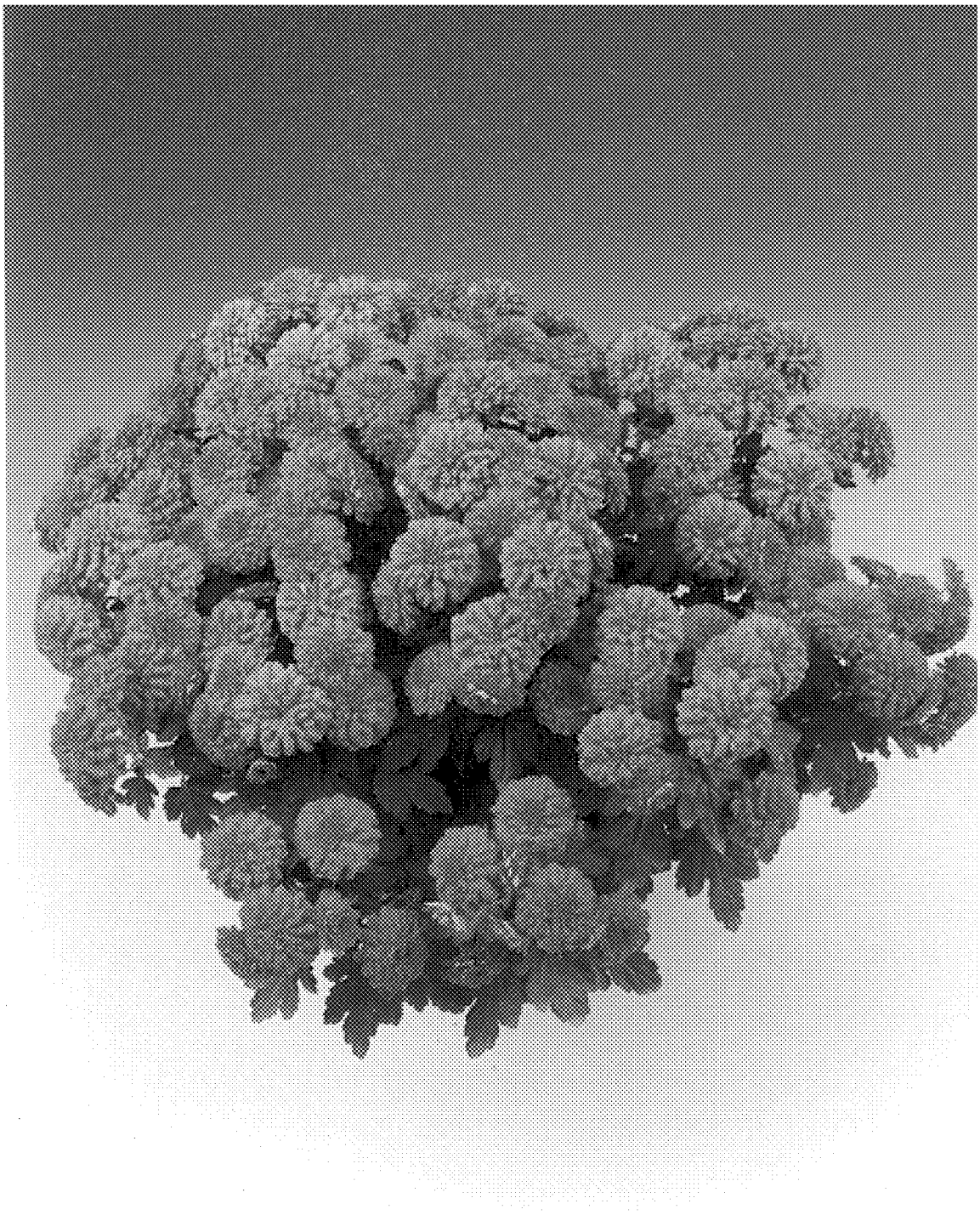
FIG. 1 is a whole plant view of the new cultivar grown in a pot.
Figure 2:
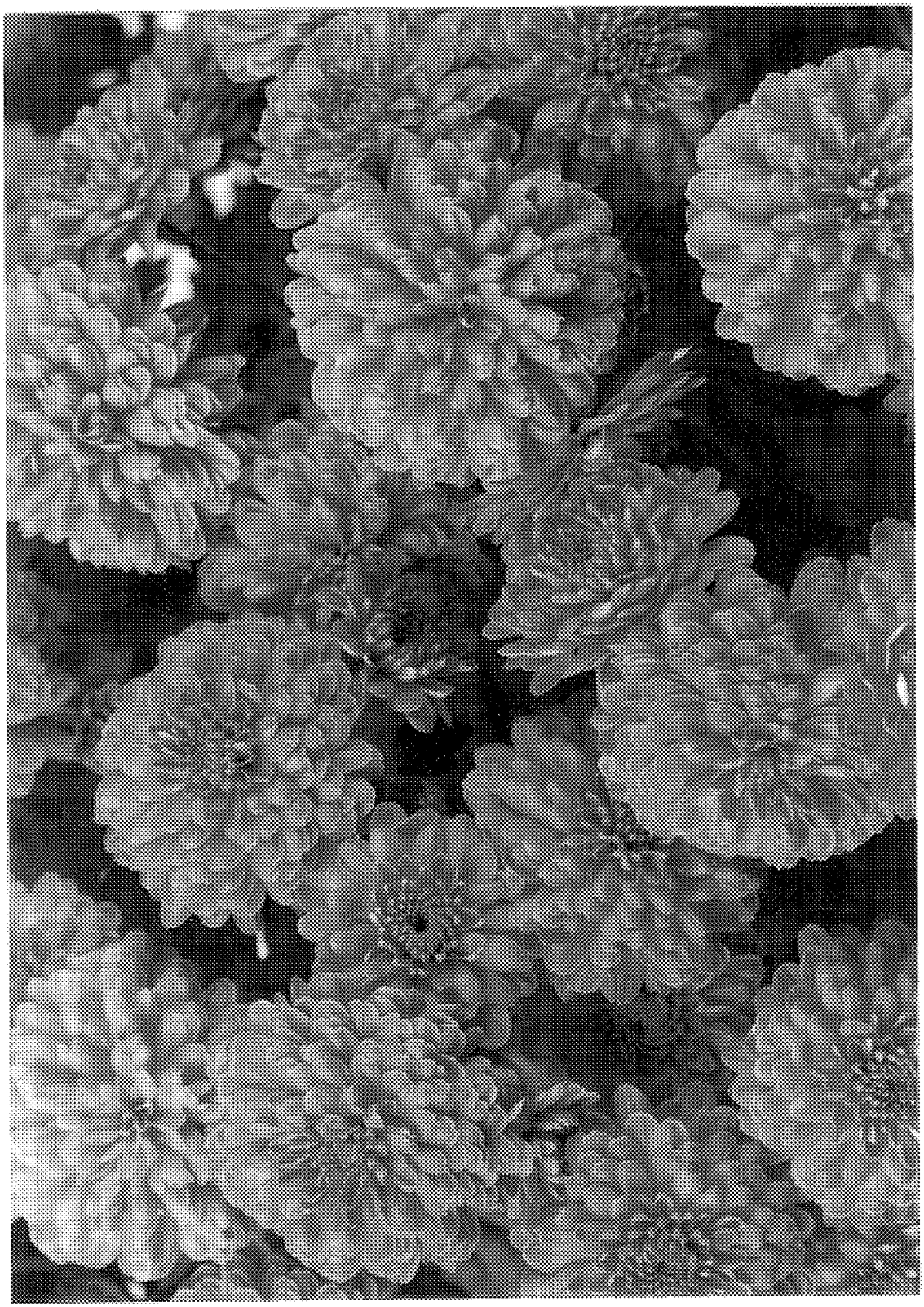
FIG. 2 is a closer view, showing inflorescence characteristics of the new cultivar in greater detail.

The following description of the new variety is of specimens grown in a greenhouse in Ventura County, Calif. in the month of October. 'Ibis' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once ten days after planting and can produce about 3 breaks per pinch. It has been observed that the shelf life of 'Ibis' is about 23 days with the response time of about 7 weeks. No treatment with growth retardant is required. Useful growing conditions include night temperature of about 64°–66° F., day temperature of about 80°–85° F. and about 5,000 foot-candles of light.

Plant:

*Habit.*—Loose, open and spreading.
*Height.*—About 25 cm.
*Number of breaks from pinch.*—About 3.
*Typical container sizes commercially grown in.*—6" pots, 1 gallon and 3 gallon containers.
*Length of lateral branches.*—About 16 cm.
*Stem color.*—Near 138B.

Foliage:

*Leaf arrangement.*—Alternate.
*Number of leaver per lateral branch.*—Usually 19 fully expanded leaves.
*Leaf size.*—Length: About 6.2 cm. Width: About 3.8 cm.
*Leaf shape.*—Ovate.
*Attachment.*—Petioled.
*Leaf apex.*—Obtuse.
*Base.*—Truncate.
*Margin.*—Lobed and serrated.
*Aspect.*—Folded upwards at mid vein.
*Surface.*—Top: Coarsely pubescent. Bottom: Pubescent.
*Petiole.*—Length: About 1.7 cm. Color: Near 138B.
*Color.*—Mature leaf: Top near 137A; bottom near near 137B. Young leaf: Top near 137B; bottom near 137C.

Flower:

*Inflorescence form.*—Cyme.
*Flower form.*—Decorative.
*Number of blooms per branch.*—About 9.
*Diameter of fully expanded bloom.*—About 4.5 cm.
*Depth of fully expanded bloom.*—About 1.8 cm.
*Sepal number.*—About 20. Color: Near 137A.
*General appearance of sepals.*—Highly pubescent, thick, very little membrane.
*Peduncle.*—Length: About 4.5 cm average around center of flower stem. Habit: Upright. Surface: Highly pubescent. Strength: Strong at base, becoming very weak at attachment to flower.
*Flower bud shape.*—Flattened sphere.
*Diameter.*—About 0.8 cm.
*Height.*—About 0.4 cm.
*Ray florets.*—Number per flower: About 250. Shape: Oblong. Apex: Obtuse, 3 lobed. Base: Truncate.

Margin: Entire. Aspect: Slightly reflexed back. Length: About 2 cm. Width: About 0.7 cm.

*Disc florets.*—Number per flower: About 5. Shape: Tubular. Margin: Entire. Length: About 0.5 cm. Width: About 0.1 cm.

*Fragrance.*—Very strong.

Flower color:

*General flower coloration.*—Magenta with very slight coral appearance in center, near 35B.

*Ray florets, top side.*—Immature: Near 64A, white streaks at base. Mature: Near 64A. Fading: Near 70B.

*Ray floret, under side.*—Immature: Near 11D, streaks and tip near 64A. Mature: Near 72B, faint white streaks.

*Disc florets.*—Mature: Near 16A tip, near 11D base.

*Changes as the flower ages.*—Flower form becomes more rounded. Color fades very little and takes on a more purple tone.

Reproductive organs:

*Ray florets.*—Pistillate. Stigma shape: 3 forked. Stigma color: Near 8A. Style length: About 0.5 cm.

*Disc florets.*—Stigma shape: 2 forked. Stigma color: Near 7A. Style length: About 0.4 cm. Stamen number: About 5. Anther length: About 0.15 cm. Pollen color: Near 13A. Pollen quantity: Moderate in individual florets.

What is claimed is:

1. A new and distinct Chrysanthemum plant of the variety substantially as herein shown and described.

* * * * *